United States Patent [19]

Endoh et al.

[11] 4,436,812
[45] Mar. 13, 1984

[54] PROCESS OF CALIBRATING A BLOOD SUGAR ANALYZING APPARATUS

[75] Inventors: Koichi Endoh, Tokyo; Nobuhiko Tsuji; Keijiroh Nakamura, both of Yokosuka; Toshiyoshi Hamada; Keiichi Ishida, both of Tokyo, all of Japan

[73] Assignee: Fuji Electric Co., Ltd., Kawasaki, Japan

[21] Appl. No.: 313,665

[22] Filed: Oct. 21, 1981

[30] Foreign Application Priority Data

Oct. 29, 1980 [JP] Japan ............................ 55-150753
Oct. 29, 1980 [JP] Japan ............................ 55-150754
Oct. 29, 1980 [JP] Japan ............................ 55-150755
Nov. 21, 1980 [JP] Japan ............................ 55-163333
Dec. 9, 1980 [JP] Japan ............................ 55-172664

[51] Int. Cl.$^3$ ...................... G01N 33/66; G01N 35/00
[52] U.S. Cl. ...................................... 435/14; 204/403; 364/415; 364/416; 364/497; 435/3; 435/288; 435/291; 435/817; 436/50; 436/95
[58] Field of Search .................. 422/81; 435/288, 14, 435/3; 204/195 B, 1 T; 364/415, 416, 497

[56] References Cited

U.S. PATENT DOCUMENTS

3,542,662 11/1970 Hicks .............................. 435/190 X
3,920,969 11/1975 Bergla ........................ 204/195 B X
3,960,497 6/1976 Acord .

Primary Examiner—Sidney Marantz
Attorney, Agent, or Firm—Brumbaugh, Graves, Donohue & Raymond

[57] ABSTRACT

A process of calibrating a blood sugar analyzing apparatus, in which the blood sugar concentration in a blood specimen is measured with a fixed enzyme membrane sensor and corrected by calibration means, said blood sugar analyzing apparatus providing a linear relationship between measured and actual blood sugar concentrations in a range of blood sugar concentrations which are lower than a predetermined blood sugar concentration, and producing a deviation from said linear relationship in a range of blood sugar concentrations higher than said predetermined blood sugar concentration, in that said process comprises the steps of effecting a plurality of measurements of standard solutions having known low blood sugar concentrations in said blood sugar analyzing apparatus, obtaining an average value of the results of the measurements with said calibration means, determining a first correction coefficient ($k_1$) to correct a deviation of said average value from the reference blood sugar concentration, thereafter measuring a blood specimen, and multiplying the result of the measurement by said correction coefficient with said calibration means when said result of the measurement is less than said predetermined blood sugar concentration and by a second calibration coefficient ($K_2$) when the result of the measurement exceeds said predetermined blood sugar concentration.

8 Claims, 9 Drawing Figures

PROCESS OF CALIBRATING A BLOOD SUGAR ANALYZING APPARATUS

BACKGROUND OF THE INVENTION

1. Field of the Invention

The present invention relates to a process of calibrating a blood sugar analyzing apparatus having a fixed glucose oxidase membrane (also known as fixed enzyme membrane).

2. Description of the Prior Art

A blood sugar analyzing apparatus of the type described above measures the blood sugar content or glucose concentration in a blood specimen which can be, for example, total blood, blood serum or plasma of a human or animal or of a standard solution (hereinafter collectively referred to as blood specimen or the like). The apparatus supplies a glucose containing specimen to the enzyme membrane sensor in order to generate a reaction current which is proportional to the blood sugar concent.

The blood sugar analysing apparatus comprises a fixed enzyme membrane electrode for measuring the reaction current (a reduction current which flows when reducing hydrogen peroxide generated upon decomposition of the glucose by the fixed enzyme membrane), a reaction cell housing the fixed enzyme membrane electrode and the blood specimen or the like, and a liquid pump for drawing a buffer liquid for washing the reaction cell.

The blood sugar analyzing apparatus is used for clinical tests with respect to diabetes, and should preferably provide a linear relationship between actual blood sugar concentrations in blood specimens and measured blood sugar concentrations. However, in the past such a linear relationship was not possible, since beyond a certain blood sugar concentration, analyzed values are lower than actual blood sugar concentrations. No satisfactory measures have heretofore been found to correct this problem. There has been a need for a blood sugar analyzing apparatus which has good linearity between measured and actual blood sugar concentrations.

With conventional measurement processes, a complex manual adjustment operation is required in order to determine a calibration coefficient using a standard solution. There is a tendency for such a calibration coefficient to be incorrectly determined when the amounts of the samples analyzed differ since only one calibration operation is normally performed. This results in a failure to maintain a required degree of accuracy in the blood sugar measurements.

SUMMARY OF THE INVENTION

It is an object of the present invention to increase the accuracy of blood sugar measurements by improving the linearity between an actual blood sugar concentration and a measured blood sugar concentration in a blood specimen.

Another object of the present invention is to dispense with complex manual adjustment procedures and to increase the measuring accuracy of a blood sugar analyzer by eliminating error in the calibration coefficient due to the varying amounts of samples introduced.

It has now been found that the former objects can be achieved by a process in which the blood sugar concentration in a blood specimen is measured with a fixed enzyme membrane sensor and corrected by calibration means, said blood sugar analyzing apparatus providing a linear relationship between measured and actual blood sugar concentrations in a range of blood sugar concentrations which are lower than a predetermined blood sugar concentration, and producing a deviation from said linear relationship in a range of blood sugar concentrations higher than said predetermined blood sugar concentration, in that said process comprises the steps of effecting a plurality of measurements of standard solutions having known low blood sugar concentrations in said blood sugar analyzing apparatus, obtaining an average value of the results of the measurements with said calibration means, determining a first correction coefficient ($K_1$) to correct a deviation of said average value from the reference blood sugar concentration, thereafter measuring a blood specimen, and multiplying the result of the measurement by said correction coefficient with said calibration means when said result of the measurement is less than said predetermined blood sugar concentration, by a second correction coefficient ($K_2$) when the result of the measurement exceeds said predetermined blood sugar concentration. Other embodiments of the process are also described herein.

DESCRIPTION OF THE PREFERRED EMBODIMENTS

A detailed description of the present invention will be made with reference to the drawings. Although the examples use glucose, the analysis is equally applicable to other blood sugars.

Figure 1:
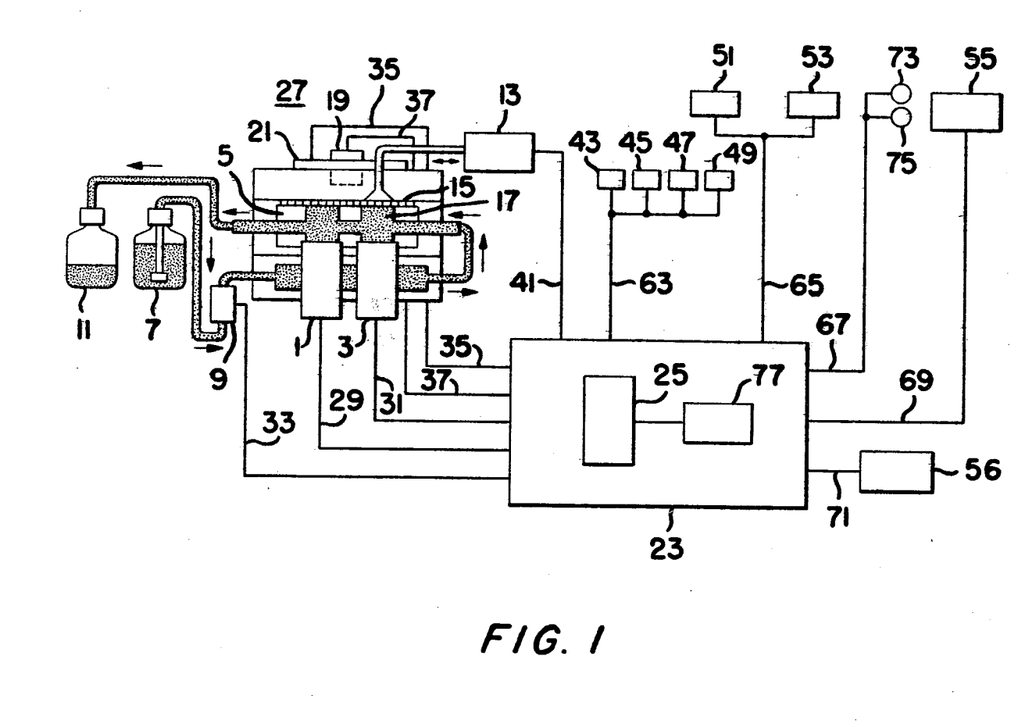
FIG. 1 is a view of the blood sugar analyzer showing an arrangement according to the present invention.

A blood sugar measurement electrode 1 for measuring a reaction current which is proportional to the blood sugar concentration comprises an electrode of platinum and silver having a membrane of glucose oxidase attached to the surface thereto. The blood sugar measurement electrode 1 and a temperature electrode 3 are disposed in a reaction cell 5. A buffer liquid 7 is delivered by a liquid pump into the cell wherein the liquid 7 washes the interior of the cell 5. After the reaction has been finished, the buffer liquid 7 is discharged as a drainage liquid 11. An air pump 13 vibrates a silicon diaphragm 15 to stir a blood specimen which has been introduced through an inlet port 17 into the cell 5, thereby making the concentration of the blood specimen in the cell 5 uniform. A temperature sensor 19 detects the temperature of the cell block. A heater 21 heats the cell block up to about the temperature of the body from which the blood specimen was taken (for example, 37° C. for a human) and, the blood in the cell 5 is maintained at a temperature equal to such temperature.

A control device 23 composed mainly of a microcomputer 25 is connected to a blood sugar analyzing unit 27 through lines 29, 31, 33, 35, 37 and 41. The control device 23 reads out a reaction current from the measurement electrode 1 over the line 29, reads out an amount of temperature compensation with respect to a measured value over the line 29, measures and controls the temperature of the cell block over the lines 35, 37, and controls operation of the liquid pump 9 and the air pump 13 over the lines 33, 41, respectively. The control device 23 is also connected to various switches 43, 45, 47, 49, 51 and 53, a display unit 55, and a printer 56 through lines 63, 65, 67, 69, 71 for controlling input and output devices. Designated at 51 is a specimen number setting switch. 53 is a standard solution value setting switch, 73 and 75 are mode setting switches for calibration and operation modes, respectively, and switches 43, 45, 47 and 49 are paper feed switches for the printer.

The blood sugar analyzing apparatus 27 first measures the known blood sugar concentration of a standard solution, and then the blood sugar analyzing apparatus is calibrated by an arithmetical unit in the control device 23 on the basis of the measurement. The measuring operation will be described in detail below.

The blood sugar analyzing apparatus is required to have linearity between the actual and measured blood sugar concentration within the range of 0 to 500 mg/dl (milligram/deciliter being a unit of blood sugar or glucose).

It has been found that when a reference solution having a concentration as high as 500 mg/dl is used for calibration, the result from analysis in the low concentration ranges will be larger than the actual value, and conversely when a reference solution having a low concentration, for example, 150 mg/dl is used, the result from analysis in the high concentration range will be smaller than an actual value.

Figure 2A:
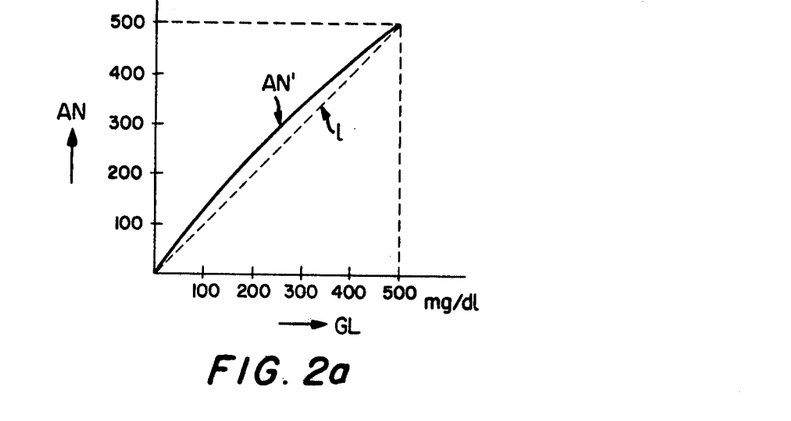
FIGS. 2(a) and 2(b) are graphs showing outputs of a blood sugar analyzer which are generated when analyzing standard solutions having glucose concentrations of 500 mg/dl and 150 mg/dl, respectively.
Figure 2B:
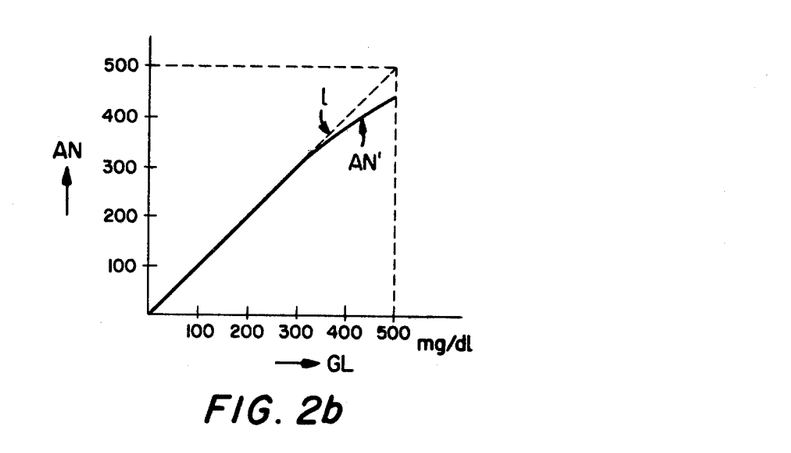

Such conditions are respectively shown in FIGS. 2(a) and 2(b). FIGS. 2(a) and 2(b) are graphs showing the relationships between glucose values GL and analyzed values AN, obtained when analyses are made using standard solutions with glucose concentrations of 500 mg/dl and 150 mg/dl, respectively. Inspection of these graphs indicates that, in FIG. 2(a) an analyzed value AN' shown by the solid line is greater than an actual value shown by the straight line l and in FIG. 2(b), there is linearity in a range of lower concentrations (0 to 300 mg/dl), but an analyzed value AN' is smaller than an actual value l in a region of higher concentrations (300 to 500 mg/dl).

The advantages of the present invention resides in the fact that the blood sugar analyzing apparatus is first calibrated using a standard solution having a lower concentration ranging from about 100 to 200 mg/dl, and the blood sugar analyzing apparatus will be recalibrated differently in a range of higher concentrations (300–500 mg/dl) in order to compensate for analyzed values which deviate negatively.

Figure 2C:
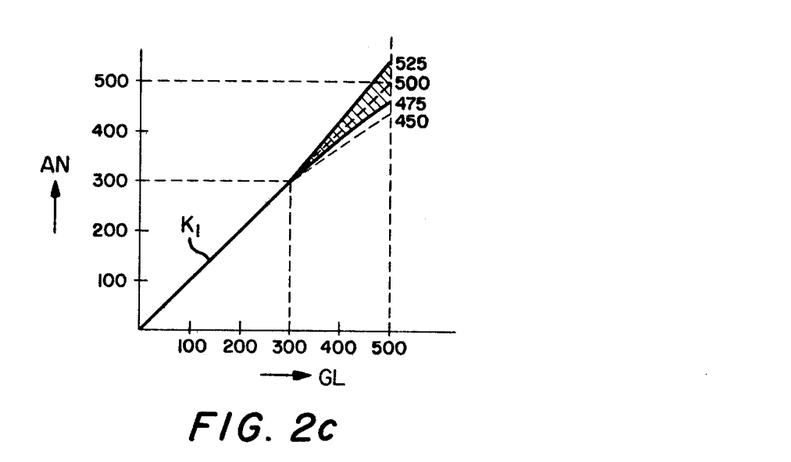
FIGS. 2(c), 3-5 are graphs illustrating the calibration processes according to the present invention.

FIG. 2(c) is a graph which illustrates the way in which the blood sugar analyzing apparatus is calibrated according to the present invention. The graph indicates actual or theoretical values for glucose GL on the horizontal axis and analyzed or measured values AN on the vertical axis, as in FIGS. 2(a) and 2(b).

When the blood sugar analyzing apparatus is calibrated using a standard solution having a low concentration, there is linearity between measured and actual blood sugar concentrations in a region of lower concentrations of 0 to 300 mg/dl as illustrated in FIG. 2(c). In this region, the analyzed results are multiplied by a correction coefficient $K_1$ to compensate for the analyzed values. Since it is known that analyzed values deviate negatively in the higher concentration range of 300 to 500 mg/dl with an average analyzed value for an actual blood sugar concentration of 500 mg/dl, results of analysis in this region which have been multiplied by the correction coefficient $K_1$ are further multiplied by a second coefficient $K_2$ of 200/175. Using this compensation process, the blood sugar concentrations of blood specimens can be analyzed more exactly in the concentration range of 0 to 500 mg/dl.

The correction coefficients $K_1$, $K_2$ used in this embodiment are as follows:

It is known that the glucose concentration in a normal healthy person ranges from 80 to 110 mg/dl, while that in a diabetic is on the order of 150 mg/dl. The blood analyzing apparatus will be calibrated using a standard solution having a glucose concentration of 150 mg/dl in order to allow the apparatus to have a maximum measuring accuracy for that glucose concentration. When the standard solution having the glucose concentration of 150 mg/dl is introduced into the reaction cell 5, the measurement electrode 1 generates an analog output XA, which is converted to a digital value XD (digit) by an analog-to-digital converter. At this time, the correction coefficient $K_1$ is given as $K_1 = 150/XD$. Thus, the coefficient $K_1$ indicates how much concentration (mg/dl) 1 digit corresponds to. The correction coefficient $K_1$ is generally expressed by:

$$K_1 = \frac{\text{Theoretical glucose concentration in the standard solution}}{\text{Digital value of the output from the measurement electrode}}$$

Therefore, when the measured glucose concentration of an unknown blood specimen has a digital value of YD digit, the actual glucose concentration is $K_1 \cdot YD$ mg/dl.

As described with reference to FIG. 2, there is linearity in the range of glucose concentrations of from 0 to 300 mg/dl. Therefore, a measured glucose concentration is compensated for by multiplying itself by the correction coefficient $K_1$ within that concentration range as described above. Use of only the correction coefficient $K_1$ in the range of from 300 to 500 mg/dl however fails to give linearity between measured and actual concentrations. In this concentration range, therefore, a measured value in excess of a standard concentration will be multiplied by the correction coefficient $K_2$ for compensation. The glucose concentration of 300 mg/dl is established as a reference value. It is assumed that when the blood sugar analyzing apparatus is to be calibrated for a standard solution having a known glucose concentration of 500 mg/dl, the apparatus indicates 475 mg/dl as an analyzed value of glucose concentration. Such analyzed value has already been multiplied by the correction coefficient $K_1$, which is a constant determined on the basis of measured data obtained in the past.

The correction coefficient $K_2$ can be given by the following equation:

$$K_2 = \frac{\text{Theoretical value} - \text{Reference value}}{\text{Analyzed value} - \text{Reference value}}$$

For the concentration of 500 mg/dl, the correction coefficient $K_2$ is as follows:

$$K_2 = \frac{500 - 300}{475 - 300} = \frac{200}{175}$$

A measured glucose concentration F in the range of 300 to 500 mg/dl is generally calculated as follows:

$$F = G + U \cdot K_2$$

where

G: reference value (for example, 300 mg/dl)
U: excess of the analyzed value AN beyond the reference value $$U = AN - G$$

Since the analyzed value of glucose concentration in the standard solution having the concentration of 500 mg/dl is 475 mg/dl, the measured glucose concentration F is given as follows:

$$F = G + U \cdot K_2$$
$$= 300 + (475 - 300) \cdot \frac{500 - 300}{475 - 300}$$
$$= 300 + 175 \cdot \frac{200}{175}$$
$$= 500 \text{ (mg/dl)}$$

With the calibration process according to the present invention, a measured value of a glucose concentration having a theoretical value of 500 mg/dl is given also as 500 mg/dl by generating a signal indicative of that value. While the foregoing calibration process has a maximum measuring accuracy for the glucose concentration of 500 mg/dl, the calibration process may have a maximum measuring accuracy for the glucose concentration of 400 mg/dl by substituting 400 for the theoretical value, 300 for the reference value, and a value measured at the time for the analyzed value in the equation to obtain the correction coefficient $K_2$.

With the present invention, as described above, measurements are compensated for in ranges of concentrations measured (for example, from 0 to 300 mg/dl and from 300 to 500 mg/dl) for obtaining high precision measurement.

Figure 3:
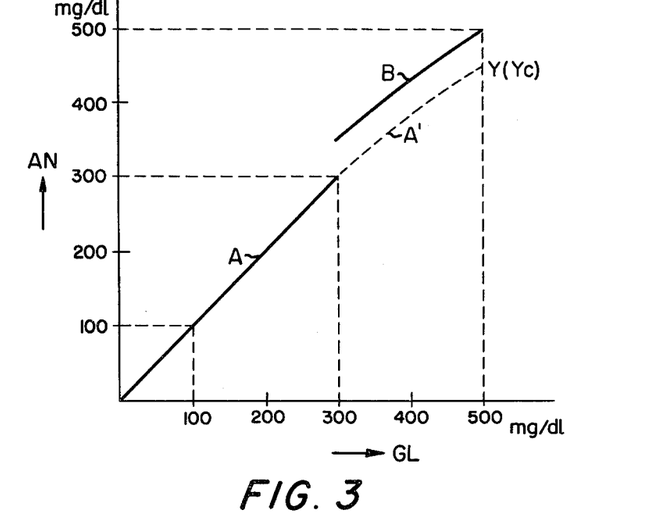

An alternate embodiment can be described with reference to FIG. 3. As in the foregoing embodiment, a measurement is made using a standard solution having a glucose concentration of 150 mg/dl, for example, and the correction coefficient $K_1$ is determined so that the result of measurement will become 150 mg/dl. Thus, the result of measurement is corrected by the correction coefficient $K_1$ so as to be on the straight line A in the range of lower concentrations from 0 to 300 mg/dl. Since no linearity is assured as shown by the line A' in the range of from 300 to 500 mg/dl, the blood sugar analyzing apparatus will be calibrated using a standard solution having a particular higher glucose concentration such for example as of 500 mg/dl. More specifically, the standard solution with the glucose concentration of 500 mg/dl is first measured, and the result is compensated for by the correction coefficient $K_1$, whereupon the compensated result is indicated by the value at the point Y on the line A'. The correction coefficient $K_2$ is determined so that the value YC at the point Y will be 500 mg/dl. The concentration region of from 300 to 500 mg/dl is now compensated for by the correction coefficient $K_2$ as illustrated by the line B. Stated otherwise, the blood sugar analyzing apparatus is calibrated at two points, i.e., at a point in the lower concentration range (from 0 to 300 mg/dl) and at a point in the higher concentration range (from 300 to 500 mg/dl), thus correcting insufficient calibration which would otherwise be effected only at one point.

The correction coefficients $K_1$, $K_2$ in this embodiment will be given as follows:

The correction coefficient $K_1$ is obtained in a manner described above.

In calculating $K_2$ the blood sugar analyzing apparatus is first calibrated using a standard solution having a theoretical glucose concentration of 500 mg/dl. It is assumed that four analyses are made and an analyzed or measured value is 480 mg/dl on the average. Using the foregoing equation, the result of measurement F can be obtained as follows:

$$F = G + U \cdot K_2$$
$$= 300 + (480 - 300) \cdot \frac{500 - 300}{480 - 300}$$
$$= 300 + 180 \cdot \frac{200}{180} = 500$$

Thus, the result of measurement is also 500 mg/dl when the theoretical glucose concentration is 500 mg/dl.

After such correction has been made, that is, after the correction coefficient $K_2 = 200/180$ has been stored in a memory in the control device 23, a blood specimen is introduced into the reaction cell. When the analyzed value is 400 mg/dl, for instance, at this time, the measured glucose concentration in the blood specimen can be calculated according to the above equation as follows:

$$F = 300 + 100 \cdot 200/180 \approx 411.1 \text{ mg/dl}$$

With the above embodiment, as described above, the blood sugar analyzing apparatus is calibrated accurately at two points in the lower and upper concentration regions for increased measuring accuracy.

Figure 4:
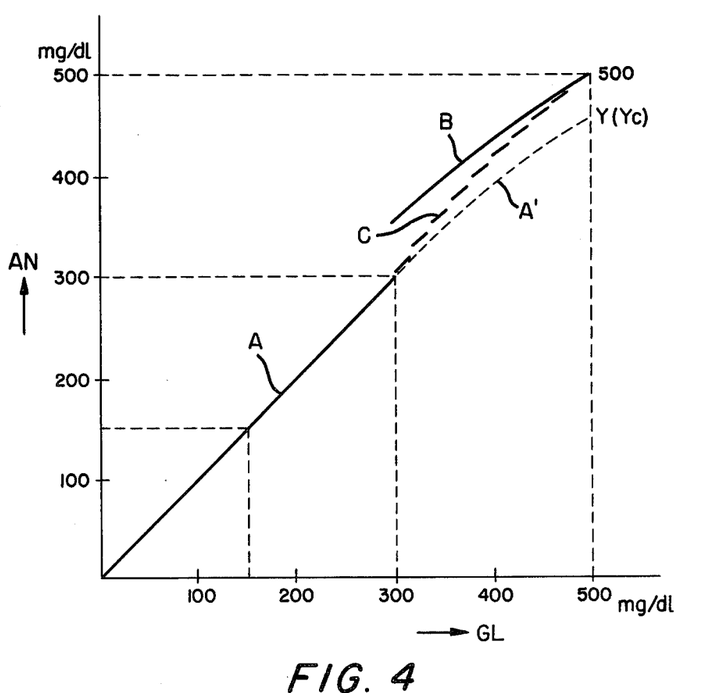

An alternate embodiment can be described with reference to FIG. 4.

With the process described with reference to FIG. 3, there is a large difference in the results of calibration in the vicinity of the glucose concentration of 300 mg/dl where there is a changeover from one correction coefficient to the other. According to the process of FIG. 4, the correction coefficient is gradually varied depending on different glucose concentration as shown by the broken line C. More specifically, the difference $(K_2 - K_1)$ between the correction coefficients $K_1$, $K_2$ is divided into n equal parts between the concentrations of 300 and 500 mg/dl, and the divided parts are proportionally distributed as $(K_2 - K_1)/n$, $2(K_2 - K_1)/n$, ... $n(K_2 - K_1)/n$. Thus an abrupt changeover from one correction coefficient to the other is eliminated in order to achieve a smooth approximation as a whole. Therefore, the i th proportional correction coefficient $K_3$ in a case where the difference between the correction coefficients $K_1$ and $K_2$ is divided into n equal parts, can be expressed as:

$$K_3 = i(K_2 - K_1)/n + K_1$$

This indicates that, in the range of from 300 to 500 mg/dl, the closer the concentration is to 300 mg/dl, the correction coefficient $K_3$ is the more influenced by the correction coefficient $K_1$, and the closer the concentration is to 500 mg/dl, the correction coefficient is the more influenced by the correction coefficient $K_2$.

The correction coefficients in this embodiment will be obtained as follows:

The correction coefficient $K_1$ can be obtained in the manner described above.

As mentioned above in calculating $K_2$ an analysis is first made of a standard solution having a theoretical glucose concentration of 500 mg/dl, the measured value is then compensated for by the correction coefficient $K_1$, and the correction coefficient $K_2$ is determined so that the corrected value YC will be 500 mg/dl. The correction coefficient $K_2$ can be expressed as follows:

$$K_2 = K_1 \cdot (500/Y_C)$$

The correction coefficient $K_3$:
As described above, this can be given by:

$$K_3 = i(K_2 - K_1)/n + K_1$$

With the above embodiment, the blood sugar analyzing apparatus is compensated for at two points in the lower and higher concentration ranges to determine the correction coefficients $K_1$, $K_2$, and an abrupt shift due to the difference between these correction coefficients is eliminated by changing the correction coefficient dependent on glucose concentrations. Calibration can thus be effected more correctly for increased degree of measuring accuracy.

Figure 5:
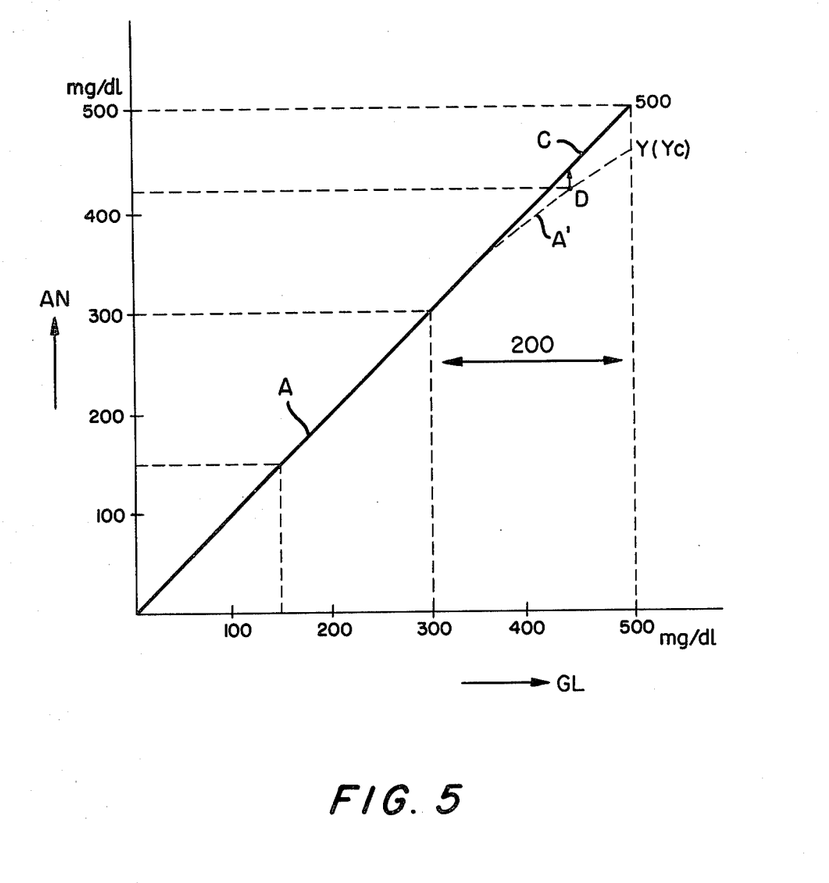

An additional alternate embodiment can be described with reference to FIG. 5.

With the process described with reference to FIG. 3, there is a large difference in results of calibration in the vicinity of the glucose concentration of 300 mg/dl where there is a changeover from one correction coefficient to the other. According to the process of FIG. 5, the correction coefficient is gradually varied dependent on different glucose concentrations as shown by the line C. More specifically, the difference $(K_2 - K_2)$ between the correction coefficients $K_1$, $K_2$ is proportionally distributed according to glucose concentrations in the range of from 300 to 500 mg/dl for continuously changing the correction coefficient. Therefore, a correction coefficient $K_3$ for a glucose concentration D determined with the correction coefficient $K_1$ in the range of from 300 to 500 mg/dl can be given as follows:

$$K_3 = \frac{(K_2 - K_1) \times \frac{D - 300}{200} + K_1}{K_1}$$

This indicates that, in the range of from 300 to 500 mg/dl, the closer the concentration is to 300 mg/dl, the correction coefficient $K_3$ is the more influenced by the correction coefficient $K_1$, and the closer the concentration is to 500 mg/dl, the correction coefficient is the more influenced by the correction coefficient $K_2$.

The correction coefficient $K_1$ can be obtained in a manner described above.

As mentioned above in calculating $K_2$ an analysis is first made of a standard solution having a theoretical glucose concentration of 500 mg/dl, the measured value is then compensated for by the correction coefficient $K_1$, and the correction coefficient $K_2$ is determined so that the corrected value $Y_C$ will be 500 mg/dl. The correction coefficient $K_2$ can be expressed as follows:

$$K_2 = K_1 \cdot (500/Y_C)$$

The correction coefficient $K_3$ can be obtained by the following equation as described above:

$$K_3 = \frac{(K_2 - K_1) \times \frac{D - 300}{200} + K_1}{K_1}$$

With this embodiment, the blood sugar analyzing apparatus is compensated for at two points in the lower and higher concentration ranges to determine the correction coefficients $K_1$, $K_2$, and an abrupt shift due to the difference between these correction coefficients is eliminated by changing the correction coefficient dependent on glucose concentrations. Calibration can thus be more correctly effected in order to increase the degree of accuracy in the measurements.

The foregoing calibration is carried out by the arithmetical unit in the control device 23 on the basis of data supplied from the measuring electrode 1 in the blood sugar analyzing apparatus. When a correction coefficient is to be determined, a plurality of measurements should preferably be made of standard solutions to obtain an average value of the measurements. Thus, different correction coefficients can be avoided which would result from calibration errors (such as due to a smaller amount of standard solution than is required). Correction coefficients determined by way of measurement and calculation are stored in a memory 77 in the control device 23. After the blood sugar analyzing apparatus has thus been calibrated, a blood specimen is measured. When the result of the measurement is less than a predetermined glucose concentration, e.g., 300 mg/dl, the result of the measurement is multiplied by the correction coefficient $K_1$. When the result of the measurement exceeds the glucose concentration of 300 mg/dl, the excess is multiplied by another correction coefficient $K_2$ or $K_3$ for thereby compensating for the measurement. The result thus corrected is indicated on the display 55, and printed on the printer 56 as desired.

An additional alternate embodiment can be described with reference to FIG. 7.

Figure 6:
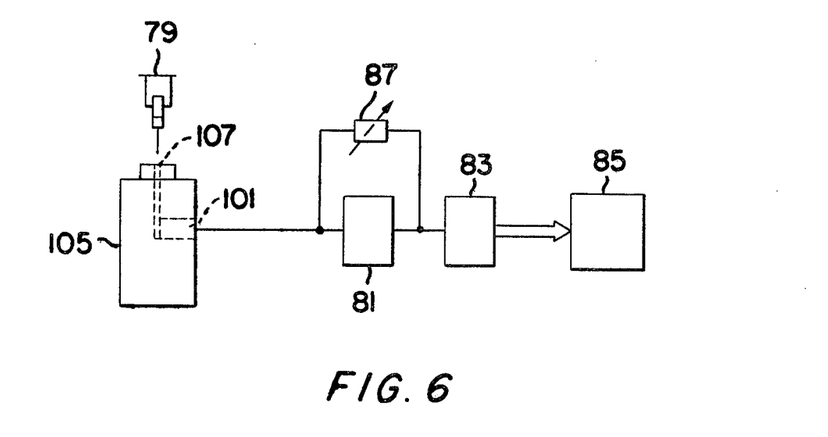
FIG. 6 is a block diagram showing a conventional process of determining an average value of a plurality of measurements.

A conventional measurement block 105 illustrated in FIG. 6 has a fixed enzyme membrane sensor 101 mounted therein and an inlet port 107 through which a standard solution or a blood specimen is introduced from an injector 79. A reaction current from the sensor 101 is amplified by an amplifier 81 and converted to a corresponding voltage, which is in turn converted by an analog-to-digital converter 83 to a digital signal, which is then supplied to a control circuit 85. Taking into consideration the conversion ability of the analog-to-digital converter 83, the output (reaction quantity) from the sensor 101 is adjusted by a gain-adjusting variable resistor 87 for the amplifier 81 so as to be indicative of 1 mg/dl (mg/dl indicates a unit of glucose concentration) when the voltage is 1 mV, for example. The input level of the analog-to-digital converter 83 is controlled to determine a conversion coefficient.

Such a conversion or calibration coefficient is obtained by measuring a standard solution in advance, and comparing a digital reaction quantity supplied through analog-to-digital conversion from the sensor with fixed data (indicative of the glucose concentration in the standard solution) given by a digital switch. As an example, assuming that a measured value of 100 mg/dl is obtained of the concentration of a standard solution which is actually 150 mg/dl, a conversion or calibration coefficient is 150/100 (1.5).

However, the foregoing process is disadvantageous in that a complex manual procedure is necessary to adjust the variable resistor 87. The variable resistor must be of high precision and hence is uneconomical.

It has therefore, been proposed that a microcomputer be incorporated in the control circuit 85 to store therein fixed data for the foregoing conversion and calibration, and such fixed data be compared with a digital value obtained by way of analog-to-digital conversion for automatic determination of a converted value.

With such a proposal, however, there is a tendency for a calibration coefficient to be incorrectly determined when the introduced samples vary in amount, since only one calibration operation is normally effected for conversation.

Figure 7:
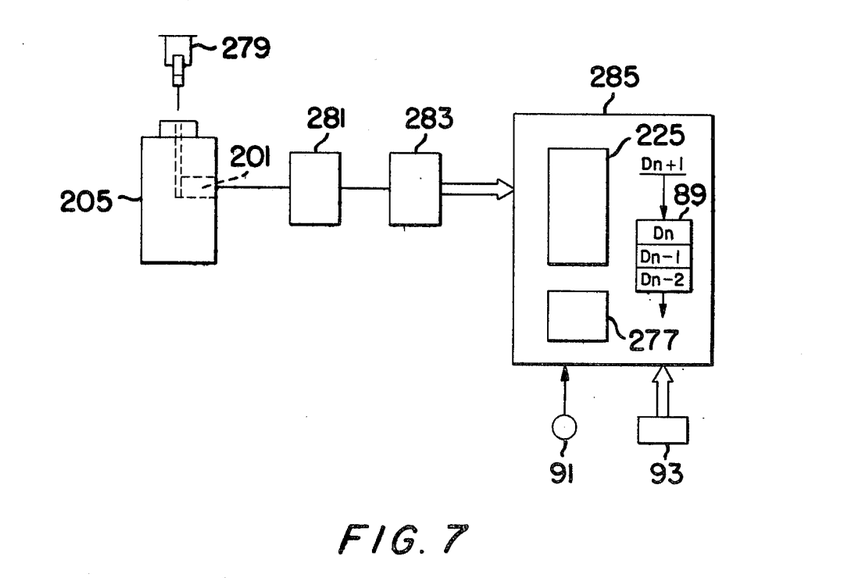
FIG. 7 is a block diagram explaining a process according to the present invention for determining an average value of a plurality of measurements.

Identical parts shown in FIG. 7 are denoted by reference characters in FIGS. 1 and 6 preceded by the number 2.

In FIG. 7, a control circuit 285 is comprised of a microcomputer 225, a memory 227, a shift register 89 and other components, the shift register 89 being incorporated according to the present invention.

A procedure for determining a calibration coefficient will be described below.

A standard solution is introduced, and a calibration button 91 is activated to instruct the control circuit 285 to enter a calibration mode of operation. At the same time, the glucose concentration in the standard solution, which is written on a bottle containing the solution, is set by a standard solution setting switch 93. As a reaction starts upon introduction of the standard solution, the control circuit 285 periodically reads out a reaction current which is supplied through the amplifier 281 and the analog-to-digital converter 283, and detects a reaction starting time and a reaction ending time at which the reaction is settled under a constant condition. Then, the control circuit 285 compares a digital quantity at the reaction ending time with fixed data established by the standard solution setting switch 93, calculates a conversion coefficient with which the output from the sensor 101 is to be converted to a glucose concentration, and stores the conversion coefficient $D_{n-2}$ in the shift register 89. The foregoing operation is repeated to determine conversion coefficients $D_{n-1}, D_n, D_{n+1}, \ldots$, which are stored in the shift register 89. The conversion coefficients thus stored are read out as desired, and an arithmetic mean value of these conversion coefficients is determined according to the following expression: $(D_{n-2}+D_{n-1}+ \ldots D_{n-m+1})/m$. The average value thus obtained serves as a final calibration coefficient and is stored.

Thereafter, a blood specimen is measured for a glucose concentration, which is corrected by the above calibration coefficient.

While the blood specimen is being measured, the calibration button 91 is left unactivated.

With the process described with reference to FIG. 7, conversion coefficients obtained by making a plurality of measurements of a standard solution are averaged to determine a calibration coefficient, which is therefore reliable and gives rise to an increased measuring accuracy.

The above process is advantageous in that a manual adjustment operation for a variable resistor is unnecessary, and an error in the calibration coefficient is reduced which would otherwise result from different amounts of standard solution introduced.

We claim:

1. A process of calibrating a blood sugar analyzing apparatus and measuring the blood sugar concentration in a blood specimen, wherein, the blood sugar concentration in the blood specimen is measured with a fixed enzyme membrane sensor and corrected by calibration means, said blood sugar analyzing apparatus providing a linear relationship between measured and actual blood sugar concentrations in a first range of blood sugar concentrations which are lower than a predetermined blood sugar concentration, and producing a deviation from said linear relationship in a second range of blood sugar concentrations higher than said predetermined blood sugar concentration, said process comprising the steps of:

measuring at least one standard solution having a known blood sugar concentration in said first range and storing the result of said measurement in storage means in said blood sugar analyzing apparatus, calculating a first correction coefficient in dependence on the stored measured value and the known blood sugar concentration from the reference blood sugar concentration in said first range, and storing said first correction coefficient in storage means, measuring at least one standard solution having a known concentration in said second range and storing the result of said measurement in storage means in said blood sugar analyzing apparatus, calculating a second correction coefficent in dependence on the stored measured value and the known blood sugar concentration in said second range and storing said second correction coefficient in storage means, and measuring a blood specimen and calculating the result of the measurement by using said first correction coefficient when said result of the measurement is less than said predetermined blood sugar concentration and by using said second correction coefficient when the result of the measurement exceeds said predetermined blood sugar concentration to thereby obtain a more accurate value of the blood sugar concentration in the blood specimen over the entire range of blood sugar concentration values than by using only one correction coefficient over the entire range of blood sugar concentration values.

2. The process according to claim 1 wherein the step of calculating a second correction coefficient (K2) is in accordance with the formula:

$K2$=(Known blood sugar concentration of calibration specimen in the second range)−(predetermined blood sugar concentration value)/(measurement result of said second calibration specimen)−(predetermined blood sugar concentration value), and wherein the step of calculating the blood sugar value (F) when the measured value exceeds said predetermined blood sugar concentration value is in accordance with the formula:

$$F = \text{(predetermined blood sugar value)} + ((\text{measured value} - \text{predetermined blood sugar value}) \times (K2)).$$

3. The process according to claim 1 wherein the step of measuring at least one standard solution in said first range comprises measuring a plurality of standard solutions having the same known blood sugar concentration values, calculating a correction coefficient for each standard solution, and calculating a first average correction coefficient value, and wherein the step of measuring the blood specimen comprises using the first average correction coefficient when the result of said measurement is less than said predetermined blood sugar concentration.

4. The process according to claim 1 wherein the step of measuring at least one standard solution in said second range comprises measuring a plurality of standard solutions having the same known blood sugar concentration values, calculating a correction coefficent for each standard solution, and calculating a second average correction coefficient value, and wherein the step of measuring the blood specimen comprises using the second average correction coefficient when the result of said measurement is greater than said predetermined blood sugar concentration.

5. The process according to claim 1 wherein the step of calculating a first correction coefficient (K1) is in accordance with the formula:

$$K1 = \text{(Known blood sugar concentration of calibration specimen in the first range)} / \text{(measurement result of said first calibration specimen)},$$

and wherein the step of calculating the blood sugar value (F) when the measured value is less than the predetermined blood sugar value is in accordance with the formula:

$$F = \text{(measured value)} \times (K1).$$

6. The process according to claim 5 wherein the step of calculating a second correction coefficient (K2) is in accordance with the formula:

$$K2 = \text{(Known blood sugar concentration of calibration specimen in the second range)} / \text{(measurement result of said second calibration specimen)},$$

and wherein the step of calculating the blood sugar value (F) when the measured value exceeds said predetermined blood sugar concentration value is in accordance with the formula:

$$F = \text{(measured value)} \times (K2).$$

7. The process according to claim 5 wherein the step of calculating a second correction coefficient (K2) is in accordance with the formula:

$$K2 = (K1) \text{ (measured value/measurement result of said second calibration specimen at upper end of second range)},$$

and wherein the step of calculating the blood sugar value (F) when the measured value exceeds said predetermined blood sugar concentration value is in accordance with the formula:

$$F = \text{(measured value)} \times (K3),$$

where $K3 = K1 + i(K2 - K1)/n$, and where the second range is divided into n equal subranges and i is the number of the subrange that the measured value falls in.

8. A process of calibrating a blood sugar analyzing apparatus and measuring the blood sugar concentration in a blood specimen, wherein a blood sugar concentration in the blood specimen is measured with a glucose oxidase film sensor and corrected by calibration means, comprising the steps of:

measuring a plurality of standard solutions having known low blood sugar concentration in said blood sugar analyzing apparatus and storing the result of said measurement in storage means, calculating a plurality of conversion coefficients in dependence on the stored measured value and the known value for the standard solutions and storing said correction coefficients successively into a shift register, reading out said plurality of correction coefficients from said shift register and calculating an average value of the conversion coefficients, and correcting a result of measurement of a blood specimen using said average value correction coefficient.

* * * * *